(12) United States Patent
Melker et al.

(10) Patent No.: US 7,104,963 B2
(45) Date of Patent: Sep. 12, 2006

(54) METHOD AND APPARATUS FOR MONITORING INTRAVENOUS (IV) DRUG CONCENTRATION USING EXHALED BREATH

(75) Inventors: Richard J. Melker, Gainesville, FL (US); David G. Bjoraker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 132 days.

(21) Appl. No.: 10/054,619

(22) Filed: Jan. 22, 2002

(65) Prior Publication Data

US 2003/0139681 A1 Jul. 24, 2003

(51) Int. Cl.
- A61B 5/08 (2006.01)
- A61M 15/00 (2006.01)
- A61M 16/00 (2006.01)
- A61M 16/10 (2006.01)

(52) U.S. Cl. .................. 600/532; 600/529; 128/203.13; 128/203.12

(58) Field of Classification Search ............... 600/529, 600/531, 532, 533, 538; 73/23.3; 128/203.12, 128/203.13
See application file for complete search history.

(56) References Cited

U.S. PATENT DOCUMENTS

| | | | |
|---|---|---|---|
| 3,567,029 A | | 3/1971 | Quame |
| 3,608,546 A | | 9/1971 | Shinn |
| 3,649,199 A | * | 3/1972 | Littlejohn ................... 436/178 |
| 3,792,272 A | * | 2/1974 | Harte et al. ................. 250/343 |
| 3,877,291 A | | 4/1975 | Hoppesch et al. |
| 3,951,607 A | | 4/1976 | Fraser |

(Continued)

FOREIGN PATENT DOCUMENTS

| | | |
|---|---|---|
| DE | 19607646 A1 | 9/1997 |
| DE | 29902593 | 8/1999 |
| EP | 0 370 151 A1 | 5/1990 |
| EP | 0 979 997 A1 | 2/2000 |

(Continued)

OTHER PUBLICATIONS

Parry AD et al. (1995) "Leg ulcer odour detection identified beta–haemolytic streptococcal infection," *Journal of Wound Care*, 4:404–406.

Huang, J.W. et al. (Aug. 1, 1996) "Depth of anesthesia estimating & propofol delivery system," http://www.rpi.edu/~royr/roy descpyt.html.

(Continued)

*Primary Examiner*—Max F. Hindenburg
*Assistant Examiner*—Navin Natnithithadha
(74) *Attorney, Agent, or Firm*—Saliwanchik, Lloyd & Saliwanchik

(57) ABSTRACT

A method and system is provided for detecting the depth of anesthesia wherein at least one anesthetic agent is absorbed in a patient's bloodstream during the administration of anesthesia, which includes sampling a patient's expired breath; analyzing the breath for concentration of at least one substance indicative of the anesthetic agent using sensor technology such as free (unmetabolized) anesthetic agent or its metabolites; determining the effect of the agent based on that concentration; and determining depth of anesthesia based thereon. The method also detects endogenous compounds such as ketones and ammonia in exhaled breath as well as other pathologic organisms.

33 Claims, 4 Drawing Sheets

U.S. PATENT DOCUMENTS

| | | | |
|---|---|---|---|
| 3,955,926 A | 5/1976 | Fischer | |
| 4,150,670 A * | 4/1979 | Jewett et al. | 128/204.22 |
| 4,202,352 A | 5/1980 | Osborn | |
| 4,215,409 A | 7/1980 | Strowe | |
| 4,312,228 A | 1/1982 | Wohltjen | |
| 4,314,564 A * | 2/1982 | Albarda | 600/532 |
| 4,334,540 A | 6/1982 | Preti et al. | |
| 4,346,584 A * | 8/1982 | Boehringer | 73/23.3 |
| 4,349,626 A | 9/1982 | Labows et al. | |
| 4,361,026 A | 11/1982 | Muller et al. | |
| 4,399,686 A | 8/1983 | Kindlund et al. | |
| 4,432,226 A | 2/1984 | Dempster | |
| 4,456,014 A | 6/1984 | Buck et al. | |
| 4,534,360 A | 8/1985 | Williams | |
| 4,734,777 A | 3/1988 | Okino et al. | |
| 4,735,777 A * | 4/1988 | Mitsui et al. | 422/70 |
| 4,772,559 A | 9/1988 | Preti et al. | |
| 4,796,639 A | 1/1989 | Snow et al. | |
| 4,868,545 A | 9/1989 | Jones | |
| 4,895,017 A | 1/1990 | Pyke et al. | |
| 4,938,928 A | 7/1990 | Koda et al. | |
| 4,992,244 A | 2/1991 | Grate | |
| 5,034,192 A | 7/1991 | Wrighton et al. | |
| 5,042,501 A | 8/1991 | Kenny et al. | |
| 5,060,506 A | 10/1991 | Douglas | |
| 5,071,770 A | 12/1991 | Kolesar, Jr. | |
| 5,081,871 A | 1/1992 | Glaser | |
| 5,082,630 A | 1/1992 | Partin et al. | |
| 5,094,235 A * | 3/1992 | Westenskow et al. | 128/204.22 |
| 5,111,827 A | 5/1992 | Rantala | |
| 5,137,692 A | 8/1992 | Fritz | |
| 5,145,645 A | 9/1992 | Zakin et al. | |
| 5,167,972 A | 12/1992 | Greenberg et al. | |
| 5,179,027 A | 1/1993 | Fisher | |
| 5,252,292 A | 10/1993 | Hirata et al. | |
| 5,296,706 A | 3/1994 | Braig et al. | |
| 5,303,575 A * | 4/1994 | Brown et al. | 73/23.3 |
| 5,317,156 A | 5/1994 | Cooper et al. | |
| 5,325,704 A | 7/1994 | Mariani et al. | |
| 5,351,522 A | 10/1994 | Lura | |
| 5,361,771 A | 11/1994 | Craine et al. | |
| 5,409,839 A | 4/1995 | Balestrieri et al. | |
| 5,425,374 A * | 6/1995 | Ueda et al. | 600/532 |
| 5,447,165 A * | 9/1995 | Gustafsson | 600/532 |
| 5,453,359 A * | 9/1995 | Gargan et al. | |
| 5,465,608 A | 11/1995 | Lokshin et al. | |
| 5,466,700 A | 11/1995 | Batenhorst et al. | |
| 5,482,601 A * | 1/1996 | Ohshima et al. | |
| 5,495,744 A * | 3/1996 | Ueda et al. | |
| 5,501,212 A * | 3/1996 | Psaros | 128/205.12 |
| 5,528,924 A | 6/1996 | Wajid et al. | |
| 5,547,878 A | 8/1996 | Kell | |
| 5,558,083 A * | 9/1996 | Bathe et al. | 128/203.12 |
| 5,560,352 A | 10/1996 | Heim et al. | |
| 5,571,401 A * | 11/1996 | Lewis et al. | |
| 5,573,005 A | 11/1996 | Ueda et al. | |
| 5,573,955 A * | 11/1996 | Khanna et al. | |
| 5,605,612 A | 2/1997 | Park et al. | |
| 5,634,517 A * | 6/1997 | Linden et al. | |
| 5,645,072 A * | 7/1997 | Thrall et al. | |
| 5,716,852 A * | 2/1998 | Yager et al. | |
| 5,756,879 A | 5/1998 | Yamagishi et al. | |
| 5,771,890 A | 6/1998 | Tamada | |
| 5,776,783 A | 7/1998 | Kell | |
| 5,783,154 A | 7/1998 | Althainz et al. | |
| 5,783,449 A * | 7/1998 | Kuznetsov | |
| 5,795,787 A | 8/1998 | Silkoff et al. | |
| 5,801,297 A * | 9/1998 | Mifsud et al. | |
| 5,826,577 A * | 10/1998 | Perroz et al. | |
| 5,830,412 A | 11/1998 | Kimura et al. | |
| 5,861,254 A * | 1/1999 | Schneider et al. | |
| 5,866,434 A * | 2/1999 | Massey et al. | |
| 5,891,398 A * | 4/1999 | Lewis et al. | |
| 5,900,552 A | 5/1999 | Chu et al. | |
| 5,918,257 A | 6/1999 | Mifsud et al. | |
| 5,925,014 A * | 7/1999 | Teeple Jr. | |
| 5,928,167 A * | 7/1999 | Wagner et al. | |
| 5,932,877 A * | 8/1999 | Braig et al. | 250/343 |
| 5,945,069 A | 8/1999 | Buehler | |
| 5,950,630 A | 9/1999 | Portwood et al. | |
| 5,954,685 A | 9/1999 | Tierney | |
| 5,958,896 A * | 9/1999 | Renshaw et al. | |
| 5,962,335 A | 10/1999 | Katzman | |
| 5,971,937 A | 10/1999 | Ekström | |
| 5,996,586 A * | 12/1999 | Phillips | |
| 6,007,775 A * | 12/1999 | Yager | |
| 6,010,459 A | 1/2000 | Silkoff et al. | |
| 6,025,200 A * | 2/2000 | Kaish et al. | |
| 6,057,162 A * | 5/2000 | Rounbehler et al. | |
| 6,063,243 A * | 5/2000 | Zettl et al. | |
| 6,067,167 A * | 5/2000 | Atkinson et al. | |
| 6,074,345 A * | 6/2000 | Van Oostrom et al. | |
| 6,085,576 A | 7/2000 | Sunshine et al. | |
| 6,094,681 A * | 7/2000 | Shaffer et al. | |
| 6,097,485 A * | 8/2000 | Lievan | |
| 6,120,443 A * | 9/2000 | Cohen-Laroque | |
| 6,131,571 A * | 10/2000 | Lampotang et al. | |
| 6,136,801 A | 10/2000 | Kell | |
| 6,153,147 A * | 11/2000 | Craig | |
| 6,180,414 B1 | 1/2001 | Katzman | |
| 6,186,977 B1 | 2/2001 | Andrews et al. | |
| 6,190,858 B1 * | 2/2001 | Persaud et al. | |
| 6,203,814 B1 * | 3/2001 | Fisher et al. | |
| 6,216,690 B1 | 4/2001 | Keitel et al. | |
| 6,221,026 B1 * | 4/2001 | Phillips | 600/532 |
| 6,234,006 B1 * | 5/2001 | Sunshine et al. | |
| 6,237,397 B1 * | 5/2001 | Shinar et al. | |
| 6,244,096 B1 | 6/2001 | Lewis et al. | |
| 6,248,078 B1 * | 6/2001 | Risby et al. | 600/529 |
| 6,251,082 B1 | 6/2001 | Rayburn | |
| 6,261,783 B1 * | 7/2001 | Jayasena et al. | |
| 6,264,913 B1 * | 7/2001 | Wagner | |
| 6,277,081 B1 * | 8/2001 | Susi et al. | 600/532 |
| 6,283,953 B1 * | 9/2001 | Ayer et al. | |
| 6,303,316 B1 * | 10/2001 | Kiel et al. | |
| 6,305,212 B1 | 10/2001 | Drzewiecki | |
| 6,312,390 B1 * | 11/2001 | Phillips | |
| 6,319,724 B1 | 11/2001 | Lewis et al. | |
| 6,328,708 B1 * | 12/2001 | Georgieff | 604/26 |
| 6,341,520 B1 * | 1/2002 | Satoh et al. | 73/23.35 |
| 6,363,772 B1 | 4/2002 | Berry | |
| 6,387,329 B1 * | 5/2002 | Lewis et al. | |
| 6,399,302 B1 * | 6/2002 | Lannigan et al. | |
| 6,416,479 B1 * | 7/2002 | Seidman | |
| 6,455,319 B1 * | 9/2002 | Lewis et al. | |
| 6,467,333 B1 * | 10/2002 | Lewis et al. | |
| 6,479,019 B1 * | 11/2002 | Goldstein et al. | |
| 6,495,824 B1 * | 12/2002 | Atkinson | |
| 6,511,453 B1 * | 1/2003 | Georgieff | 604/26 |
| 6,558,626 B1 * | 5/2003 | Aker et al. | |
| 6,589,727 B1 * | 7/2003 | Klenerman et al. | |
| 6,597,438 B1 * | 7/2003 | Cabuz et al. | |
| 6,598,459 B1 * | 7/2003 | Fu | |
| 6,599,253 B1 * | 7/2003 | Baum et al. | 600/532 |
| 6,599,281 B1 * | 7/2003 | Struys et al. | 604/503 |
| 6,620,800 B1 | 9/2003 | Roberts, II | |
| 6,631,333 B1 | 10/2003 | Lewis et al. | |
| 6,680,377 B1 | 1/2004 | Stanton et al. | |
| 6,727,075 B1 | 4/2004 | Fitzgerald et al. | |
| 6,755,783 B1 | 6/2004 | Cosentino et al. | |
| 2001/0021815 A1 | 9/2001 | Katzman et al. | |

| | | | |
|---|---|---|---|
| 2001/0046674 | A1 | 11/2001 | Ellington |
| 2001/0050228 | A1 | 12/2001 | Jaeger |
| 2001/0055544 | A1 | 12/2001 | Copp |
| 2002/0007249 | A1 | 1/2002 | Cranley et al. |
| 2002/0007687 | A1 | 1/2002 | Zimmerman et al. |
| 2002/0014236 | A1 | 2/2002 | Dittmann et al. |
| 2002/0034757 | A1 | 3/2002 | Cubicciotti |
| 2002/0068295 | A1 | 6/2002 | Madou et al. |
| 2002/0177232 | A1 | 11/2002 | Melker et al. |
| 2003/0004426 | A1 | 1/2003 | Melker et al. |
| 2003/0059820 | A1 | 3/2003 | Vo-Dinh |
| 2003/0087239 | A1 | 5/2003 | Stanton et al. |
| 2003/0119065 | A1 | 6/2003 | Lin et al. |
| 2003/0139681 | A1 | 7/2003 | Melker et al. |
| 2003/0216660 | A1 | 11/2003 | Ben-Oren et al. |
| 2004/0027246 | A1 | 2/2004 | Aguglia |
| 2004/0101477 | A1 | 5/2004 | Leyland-Jones |
| 2005/0065446 | A1 | 3/2005 | Talton |

FOREIGN PATENT DOCUMENTS

| | | |
|---|---|---|
| GB | 829409 A | 3/1960 |
| GB | 2 309 166 A | 7/1997 |
| GB | 2 329 245 A | 3/1999 |
| JP | 08313407 A | 11/1996 |
| RU | 2104535 C1 | 2/1998 |
| WO | WO 87/02773 A1 | 5/1987 |
| WO | WO 92/10749 | 6/1992 |
| WO | WO 95/08113 A1 | 3/1995 |
| WO | WO 95/31718 | 11/1995 |
| WO | WO 99/12471 | 3/1999 |
| WO | WO 00/25108 A1 | 5/2000 |
| WO | WO 98/57145 A1 | 5/2000 |
| WO | WO 2002/079514 A1 | 10/2000 |
| WO | WO 00/67820 | 11/2000 |
| WO | WO 00/79243 A1 | 12/2000 |
| WO | WO 03/016901 A1 | 2/2003 |
| WO | WO 03/045473 | 6/2003 |
| WO | WO 2004/065404 A1 | 8/2004 |

OTHER PUBLICATIONS

Kenny, G. "Target–controlled infusions–pharmacokinetic and pharmacodynamic variations," http://www.anaesthesiologie.med.uni–erlangen.de/esctaic97/a kenny.htm.

Chandiok S, et al. (1997) Screening for bacterial vaginosis: a novel application of artificial nose technology, *Journal of Clinical Pathology*, 50/(9):790–791.

Hanson, III, CW, Steinberger HA (Sep. 1997) "The use of a novel electronic nose to diagnose the presence of intrapulmonary infection," *Anesthesiology*, 87 (3A), Abstract A269.

Groves, W.A. et al. (1998) Analyzing organic vapors in exhaled breath using a surface acoustic wave sensor array with preconcentration: Selection and characterization of the preconcentrator adsorbent, *Analytica Chimica Acta* pp. 131–143.

Kuipers, J.A. et al. (1999) "First–pass lung uptake and pulmonary clearance of propofol," *Anesthesiology* 91:1780–1787.

Fujita, A. et al. (2000) "A Simple method for detecting plasma propofol," *Anesth. Analog* 90:1452–1454.

Fang, M. et al., "Detection of Organic Chemicals by SAW Sensor Array," *Sensors and Actuators*, 1999, vol. B56, pp. 155–157.

Frauendorf C. et al., "Detection of Small Organic Analytes by Fluorescing Molecular Switches" *Bioorganic & Medicinal Chemistry 9*, 2001, pp. 2521–2524.

Jayasena S., "Aptamers: An Emerging Class of Molecules That Rival Antibodies in Diagnostics" *Clinical Chemistry*, 1999, vol. 45, No. 9, pp. 1628–1650.

Stojanovic M. et al., "Aptamer–Based Folding Fluorescent Sensor for Cocaine" *Journal of the American Chemistry Society*, 2001, vol. 123, pp. 4928–4931.

Wohltjen, H. et al., "Determination of Partition Coefficients from Surface Acoustic Wave Vapor Senor Responses and Correlation with Gas—Liquid Chromatographic Partition Coefficients", *Anal. Chem.*, (1988), 60: 869–875.

Wohltjen, H. et al., "Surface Acoustic Wave Devices for Chemical Analysis", *Anal. Chem.* (1989), pp. 704A–712A, vol. 61, No. 11.

Wohltjen, H. et al., "Vapor Detection with Surface Acoustic Wave Microsensors", *Chemical Sensors and Microinstrumentation* (1989), pp. 157–175.

U.S. Appl. No. 09/708,789, filed Nov. 8, 2000, Lampotang et al.

Brody, E. N. et al., "Aptamers as Therapeutic and Diagnostic Agents," *Reviews in Molecular Biotechnology* (2000), vol. 74, pp. 5–13.

Brody et al. "The use of Aptamers in Large Arrays for Molecular Diagnostics," *Molecular Diagnosis* (1999), vol. 4, No. 4, pp. 381–388.

Dickinson, T. A. et al., "Current Trends in 'Artificial–Nose' Technology,"*Tib Tech*, 1998, 16:250–258.

Fisher et al. "A man–portable chemical sniffer utilizing Novel Fluorescent polymers for detection of ultra–trace concentrations of explosives emanating from landmines," *Nomadics Inc.* (2000), pp. 1–10.

Ganga–Zandzou, P.S. et al. "A 13C–urea breath test in children with Helicobacter pylori infection: validity of the use of a mask to collect exhaled breath sample,"*Acta Paediatr.* (2001), vol. 90, pp. 232–233.

Hammon III, W. S. et al., "Forensic GPR: Finite–Difference Simulations of Responses From Buried Human Remains," *Journal of Applied Geophysics*, (2000), 45:171–186.

Hong, C. et al., "Carbon Nanotube–Enhanced Electrochemical DNA Biosensor for DNA Hybridization Detection" (2003), *Anal. Bioanal. Chem.*, 375:287–293.

Liebich et al. "Volatile Substances in Blood Serum: a Profile Analysis and Quantitative Determination," *Journal of Chromatography* (1977), vol. 142, pp. 505–516.

Miller III, E. R. et al., "Association Between Cigarette Smoking and Lipid Peroxidation in a Controlled Feeding Study," *Circulation*, (1997), 96(4):1097–1101.

Mueller et al. "Experience in mass spectrometric identification in acute poisoning," *Beitr. Diagn. Ther, Akuter. Intox., Vortr. Symp. 4$^{th}$* (1982), pp. 126–134, ABSTRACT ONLY.

Pantarotto D. et al., "Synthesis, Structural Characterization, and Immunological Properties of Carbon Nanotubes Functionalized with Peptides" (2003), *J. Am. Chem. Soc.*, 125:6160–6164.

Pavlou and Turner. "Sniffing out the truth: Clinical Diagnosis Using the Electronic Nose," *Clin. Chem. Lab. Med.* (2000), vol. 38, No. 2, pp. 99–112.

Perri, F. "Diagnosis of *Helicobacter pylori* infection: which is best? The urea breath test," *Dig. Liver. Dis.* (2000), vol. 32, Supp. 3, pp. S196–198.

Phillips, M., "Breath Tests in Medicine," Scientific American, 1992, pp. 52–57.

Pilar Kraman, "Prescription Drug Diversion," *Trends Alert* provided by the Council of State Government at www.csg.org (Apr. 2004).

Rogers et al. "Fiber–optic biosensors based on total internal–reflection fluorescence," *American Chemical Society* (1992), Ch. 13, pp. 165–173.

Stuart, B. H. et al., "Studies of Adipocere Using Diffuse Reflectance Infrared Spectroscopy," *Vibrational Spectroscopy*, 24:233–242, (2000).

Stubbs, D. D. et al., "Investigation of Cocaine Plumes Using Surface Acoustic Wave Immunoassay Sensors,"*Anal. Chem.*, 75:6231–6235, (2003).

Tracqui, A. et al., "Systematic Toxicological Analysis Using HPLC/DAD," *Journal of Forensic Sciences* (1995), vol. 40, No. 2, pp. 254–262.

U.S. Food and Drug Administration, "FDA White Paper, Protecting the Public Health: FDA Pursues and Aggressive Enforcement Strategy," www.fda.gov/oc/whitepapers/enforce.html (Jun. 30, 2003).

U.S. Food and Drug Administration, "New FDA Initiative to Combat Counterfeit Drugs," www.fda.gov/oc/initiatives/counterfeit.backgrounder.html (Jul. 2, 2004).

United States Department of Justic, "Review of the Drug Enforcement Administration's (DEA) Control of the Diversion of Controlled Pharmaceuticals," Report Number i–2002–010 www.usdoj.gov/inspection/DEA/0210/background.htm (Sep. 2002).

Vass, A., "Beyond the Grave –Understanding Human Decomposition," *Microbiology Today*, Nov. 2001, 28:190–192.

Vass, A. et al., "Decomposition Chemistry of Human Remains: A New Methodology for Determining the Postmortem Interval," *J. Forensic Sci.*, (2002), 47(3):542–553.

Vass, A. et al., "Detection of Buried Human Remains Using Bioreporter Fluorescence," U.S. Dept. of Energy Report, Y/NSP–726 (2001).

* cited by examiner

METHOD AND APPARATUS FOR MONITORING INTRAVENOUS (IV) DRUG CONCENTRATION USING EXHALED BREATH

FIELD OF INVENTION

The present invention relates to non-invasive monitoring substance/compound concentrations in blood, and, more particularly, to a method and apparatus for the detection of such levels utilizing a breath detection system.

BACKGROUND INFORMATION

Anesthesia is extremely safe. Anesthesiologists use sophisticated technology to monitor the vital signs of and to provide respiratory and cardiovascular support for patients undergoing surgical procedures. Historically, most anesthetics were performed using inhaled agents. The depth of anesthesia induced by an inhalational anesthetic depends primarily on the partial pressure (or gas tension) of the anesthetic in the brain, and the rate of induction and recovery from anesthesia depends on the rate of change of partial pressure in the brain. The depth of anesthesia reflects the degree of blockade of sensory, reflex, mental, and motor functions, which can be achieved by using either inhalational or intravenous (IV) anesthetics, or combination of both agents. With inhalation agents, the concentration of drug delivered can be precisely metered and the variation between patients in the depth of anesthesia resulting from known concentrations of inhaled agents is relatively narrow, permitting the anesthesiologist to confidently assume a particular level of anesthesia based on the concentration of anesthetic gas delivered. Occasionally, this is not the case, and patients have recall of events that occurred during the surgical procedure. Recall is usually not a significant issue, however, in instances where a muscle relaxant is also given, rendering the patient paralyzed, an inadequate depth of anesthesia may result in the patient perceiving pain and being unable to alert the anesthesiologist. Also, the patient may remember conversation or other unpleasant events during his surgery. This rare, but dramatic event can be psychologically devastating to a patient. Because of these events, and the desire to more closely titrate the depth of anesthesia, a number of devices have been developed that purport to monitor a patient's depth of anesthesia by processing electrical signals produced by the brain. Studies have shown these technologies tend to be imprecise, and anesthetic agent specific. A more specific method of determining depth of anesthesia, or alternatively the blood concentration of anesthetic agents is desirable. Recently other methods of providing anesthesia, including IV anesthesia, have been popularized, and offer advantages over inhalation anesthetics.

Among the newer anesthetic techniques is total IV anesthesia (TIVA) which uses IV agents in place of the conventional vaporized inhalants. Unlike inhaled anesthetics, IV anesthetics produced a wider range of anesthesia for a specific drug dosage (less predictable), owing at least in part to interactions with other drugs, competition for binding sites in the blood and other body tissues, and genetic variation in the enzymes responsible for drug metabolism. At present, a major impediment to the wider use of IV anesthetics, rather than inhaled anesthetics, has been the inability to precisely determine the quantity of drug required to provide a sufficient "depth of anesthesia" without accumulating an excessive amount.

Propofol, for example, is an agent that is widely used as a short acting IV anesthetic. Its physiochemical properties are hydrophobic and volatile. It is usually administered as a constant IV infusion in order to deliver and maintain a specific plasma concentration. Although the metabolism is mainly hepatic and rapid, there is significant interpatient variability in the plasma concentration achieved with a known dose. However, the depth of anesthesia for a known plasma concentration is far less variable and it is therefore highly desirable to be able to evaluate plasma concentrations in real time to accurately maintain anesthetic efficacy. ["A Simple Method for Detecting Plasma Propofol," Akihiko Fujita, MD, et al., Feb. 25, 2000, International Anesthesia Research Society]. The authors describe a means to measure plasma rather than total propofol using headspace—GC with solid phase microextraction. This is preferable since plasma (free) propofol is responsible for the anesthetic effect. Prior methods of monitoring propofol concentration in blood include high performance liquid chromatography (HPLC) and gas chromatography (GC). It has been reported that 97%–99% of propofol is bound with albumin and red blood cells after IV injection, and the remainder exists in blood as a free type. HPLC and GC detect the total propofol concentration, which does not correlate as well with the anesthetic effect as the plasma propofol level.

Propofol may also be monitored in urine. Metabolic processes control the clearance of propofol from the body, with the liver being the principal eliminating organ. ["First-pass Uptake and Pulmonary Clearance of Propofol," Jette Kuipers, et al., Anesthesiology, V91, No.6, December 1999]. In a study, 88% of the dose of propofol was recovered in urine as hydroxylated and conjugated metabolites.

The aim of any dosage regimen in anesthesia is to titrate the delivery rate of a drug to achieve the desired pharmacolgic effect for any individual patient while minimizing the unwanted toxic side effects. Certain drugs such as propofol, afentanil and remifentanil have a close relationship between blood concentration and effect; thus, the administration of the drug can be improved by basing the dosage regimen on the pharmacokinetics of the agent. [Kenny, Gavin, *Target-Controlled Infusions—Pharmacokinetics and Pharmodynamic Variations,* http://www.anaesthesiologie.med.unierlangen.de/esctaic97/a_Kenny.htm]. Target controlled infusion (TCI) is one means for administering an intravenous anesthesia agent using a computer to control the infusion pump. Using a computer with a pharmacokinetic program permits control of a desired plasma concentration of an agent, such as propofol. The systems do not sample the blood in real-time, but use previously acquired population kinetics to provide a best estimate of the predicted blood concentration. However, even if TCI systems produced the exact target concentrations of blood concentration, it would not be possible to know if that concentration was satisfactory for each individual patient and for different points during the surgical procedure.

Among the technologies used to process and monitor electrical brain signal is BIS (Bispectral Index Monitor) monitoring of electroencephalography (EEG) data. It is an indirect monitor of depth of anesthesia. The BIS monitor translates EEG waves from the brain into a single number—depicting the depth of anesthesia on a scale from 1 to 100. In addition, neural networks have been used to classify sedation concentration from the power spectrum of the EEG signal. However, this technology is costly and not entirely predictive.

Artificial neural networks have also been developed which use the patient's age, weight, heart rate, respiratory rate, and blood pressure to predict depth of anesthesia. The networks integrate physiological signals and extract meaningful information. Certain systems use mid-latency auditory evoked potentials (MLAEP) which are wavelet transformed and fed into an artificial neural network for classification in determining the anesthesia depth. [Depth of Anesthesia Estimating & Propofol Delivery System, by Johnnie W. Huang, et al., Aug. 1, 1996, http://www.rpi.edu/~royr/roy_descpt.html].

An apparatus and method for total intravenous anesthesia delivery is also disclosed in U.S. Pat. No. 6,186,977 to Andrews. This patent describes a method in which the patient is monitored using at least one of electrocardiogram (EKG), a blood oxygen monitor, a blood carbon dioxide monitor, inspiration/expiration oxygen, inspiration/expiration carbon dioxide, a blood pressure monitor, a pulse rate monitor, a respiration rate monitor, and a patient temperature monitor.

Accordingly, there is a need in the art for a more predictive method and apparatus for the non-invasive detection of drug concentration in blood, especially anesthetic agents.

BRIEF SUMMARY OF THE INVENTION

The present invention solves the needs in the art by providing a method and apparatus for non-invasive monitoring of substance/compound concentration in blood, and, more particularly, to a method and apparatus for the detection, quantitation and trending of IV delivered drug concentration utilizing a breath detection system. The method includes the steps of receiving exhaled breath of a subject and measuring the concentration of one or more components in the exhaled breath. These measured components can then be used to monitor depth of anesthesia, for example.

A variety of systems have been developed to collect and monitor exhaled breath components, particularly gases. For example, U.S. Pat. No. 6,010,459 to Silkoff describes a method and apparatus for the measurement of components of exhaled breath in humans. Various other apparatus for collecting and analyzing expired breath include the breath sampler of Glaser et al, U.S. Pat. No. 5,081,871; the apparatus of Kenny et al, U.S. Pat. No. 5,042,501; the apparatus for measuring expired breath of infants of Osborn, U.S. Pat. No. 4,202,352; the blood alcohol concentration measuring from respiratory air method of Ekstrom, U.S. Pat. No. 5,971,937, and the instrument for parallel analysis of metabolites in human urine and expired air of Mitsui et al., U.S. Pat. No. 4,734,777. Pulmonary diagnostic systems including computerized data analysis components also are known, e.g., Snow et al., U.S. Pat. No. 4,796,639.

One particular application of the present invention is for predicting the depth of anesthesia utilizing a breath detection system. It has been shown that there is a good correlation between blood concentration of anesthetic agents (e.g., propofol) and depth of anesthesia.

Since there is no direct on-line method to continuously monitor blood concentration of agents, in that the blood and exhaled concentration are relatively proportional, the method of the present invention will provide a more predictive method to monitor depth of anesthesia by monitoring breath rather than blood.

The method of the present invention may also be used to monitor perflubron concentration. Emulsified perflubron is one of a class of compounds used to deliver oxygen in anemic patients as a substitute for hemoglobin.

The invention apparatus provides a device for measuring components of exhaled breath of a subject in the methods described above. This device includes sensor technology; such as the commercial devices referred to as "artificial noses" or "electronic noses" to non-invasively monitor such concentration. Other sensors may include any of those well known in the art such as metal-insulator-metal ensemble (MIME) sensors, cross-reactive optical microsensor arrays, and fluorescent polymer films, and surface enhanced raman spectroscopy (SERS). The invention further includes a reporting system capable of tracking concentration (remote or proximate) and providing the necessary outputs, controls, and alerts.

In one example, a breath detector of the present invention would be used during delivery of total intravenous anesthesia (TIVA) to monitor drug concentration of intravenous anesthetics such as propofol by measuring propofol concentration in exhaled breath. Moreover, sensing antibiotics with the exhaled breath detection method of the present invention, would allow for use of the method as a surrogate for blood antibiotic concentration. This would also be true for a wide range of medications for which blood concentration would be valuable. Exhaled breath detection using the method of the present invention may also evaluate pharmacodynamics and pharmacokinetics for both drug studies and in individual patients. Moreover, it may be used to sense endogenous compounds such as glucose, ketones and electrolytes which are normally found in blood.

Therefore, it is an object of the present invention to non-invasively monitor substance concentration by methods including, but not limited to, sensor technology (e.g., silicon chip technology). A resulting advantage is the ability to monitor such concentration in a more cost effective and frequent manner. This method may replace the invasive practice of drawing blood to measure concentration. Moreover, measurement of medications (and other substances) in exhaled breath may prove to be a major advance in monitoring a variety of drugs, compounds, naturally occurring metabolites, and molecules.

The invention will now be described, by way of example and not by way of limitation, with reference to the accompanying sheets of drawings and other objects, features and advantages of the invention will be apparent from this detailed disclosure and from the appended claims. All patents, patent applications, provisional applications, and publications referred to or cited herein, or from which a claim for benefit of priority has been made, are incorporated by reference in their entirety to the extent they are not inconsistent with the explicit teachings of this specification.

DETAILED DESCRIPTION OF THE INVENTION

The present invention provides a method and apparatus for non-invasive monitoring substance/compound concentration in blood by utilizing a breath detection system.

One embodiment of the present invention is a method for detecting the depth of anesthesia utilizing the breath detection system of the present invention.

Figure 2:
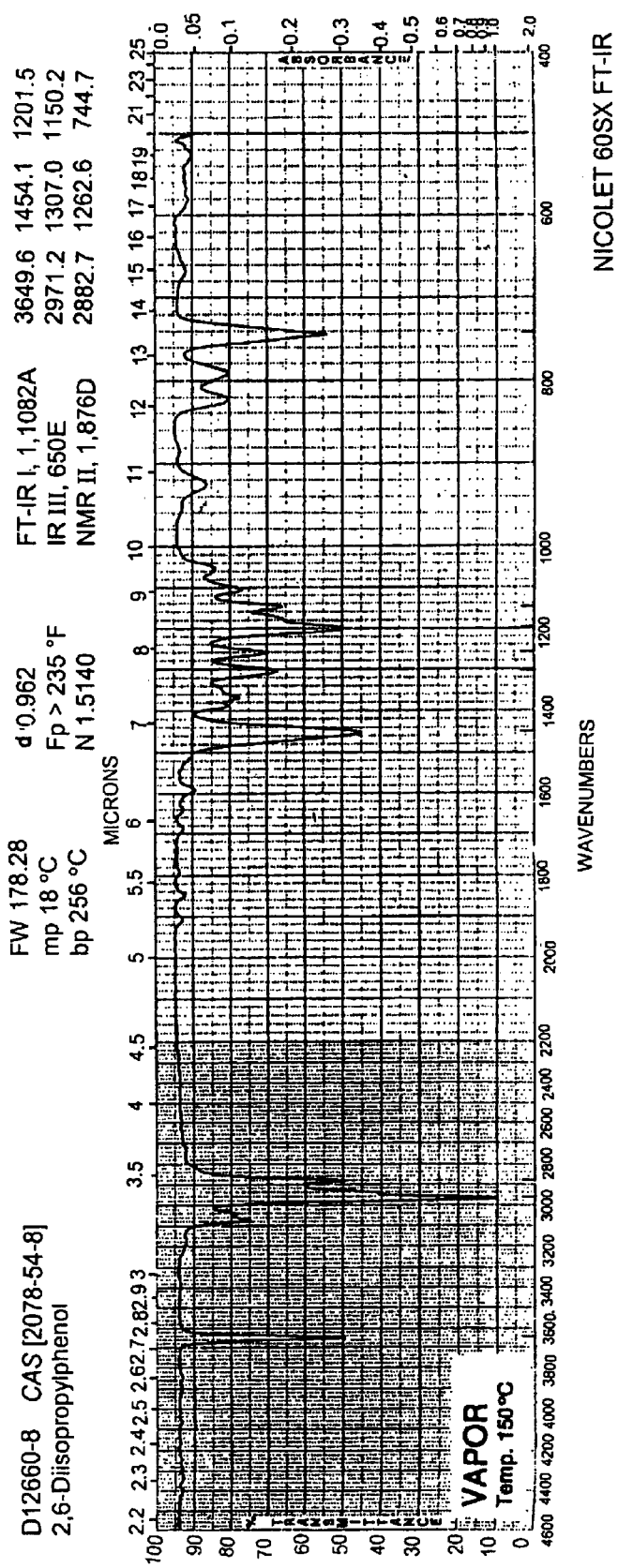
FIG. 2 shows the FT-IR signal for propofol.

During intravenous anesthesia, anesthetic agents are administered directly into a patient's bloodstream. The administered drug may bind to proteins circulating in the blood, be absorbed into fat or exist in a "free" form. Drug bound to protein or absorbed in fat does not produce a pharmacological effect and exists in equilibrium with unbound drug. Numerous factors, including competition for binding sites on the protein from other drugs, the amount of fat in the body and the amount of protein produced, determine the equilibrium between bound and unbound drug. Unbound drug may participate directly in the pharmacological effect or be metabolized into a drug that produces the effect. Metabolism of the active drug often leads to its removal from the bloodstream and termination of its effect. The drug effect can also be terminated by the excretion of the free drug. Free drug or a metabolite can be excreted in the urine or the digestive tract or in exhaled breath. The concentration in the blood (or plasma or serum) of such agents (e.g., propofol, alfentanil and remifentanil) is related to the clinical effect of the agent. FIG. 2 represents the FT-IR signal for propofol (2,6-diisopropylphenol). It has been specifically shown that there is a good correlation between blood concentration of anesthetic agents (e.g., propofol) and depth of anesthesia. Therefore, testing blood concentration is a good indicator of the effect of the agent (depth of anesthesia). Unfortunately, testing blood directly is invasive and time consuming. When a drug or its metabolite is excreted in the breath, the concentration in expired breath is proportional to the free drug or metabolite concentration in the blood and, thus, indicative of depth of anesthesia and/or the rate of drug metabolism. The metabolite measured in exhaled breath may be the active metabolite or a breakdown product of the active drug. As long as there is equilibrium between the active drug and an inactive metabolite excreted in the breath, the activity of the active drug will be known. The method of the present invention takes into account such proportional concentrations and allows for the determination of depth of anesthesia and/or the rate of metabolism of the drug by measuring concentration of unbound substances, agents and/or active metabolites in a patient's breath. The proper dosing regimen can thus be determined therefrom.

Generally, the exhalation gas stream comprises sequences or stages. At the beginning of exhalation there is an initial stage, the gas representative thereof coming from an anatomically inactive (deadspace) part of the respiratory system, in other words, from the mouth and upper respiratory tracts. This is followed by a plateau stage. Early in the plateau stage, the gas is a mixture of deadspace and metabolically active gases. The last portion of the exhaled breath comprises nothing but deep lung, so-called alveolar gas. This gas, which comes from the alveoli, is termed end-tidal gas. In one embodiment, the exhaled breath sample is collected at end-tidal breathing. Technology similar to that used for end-tidal carbon dioxide monitoring can be used to determine when the sample is collected. Airway pressure measurements afford another means of collecting samples at the appropriate phase of the respiratory cycle. Single or multiple samples collected by the side stream method are preferable, but if sensor acquisition time is reduced, in-line sampling may be used. In the former, samples are collected through an adapter at the proximal end of the endotracheal tube and drawn through thin bore tubing to the sensor chamber. Depending on the sample size and detector response time, gas may be collected on successive cycles. With in-line sampling, the sensor is placed proximal to the ET tube directly in the gas stream. Alternatively to sampling end-tidal gas, samples can be taken throughout the exhalation phase of respiration and average value determined and correlated with blood concentration.

Figure 3:
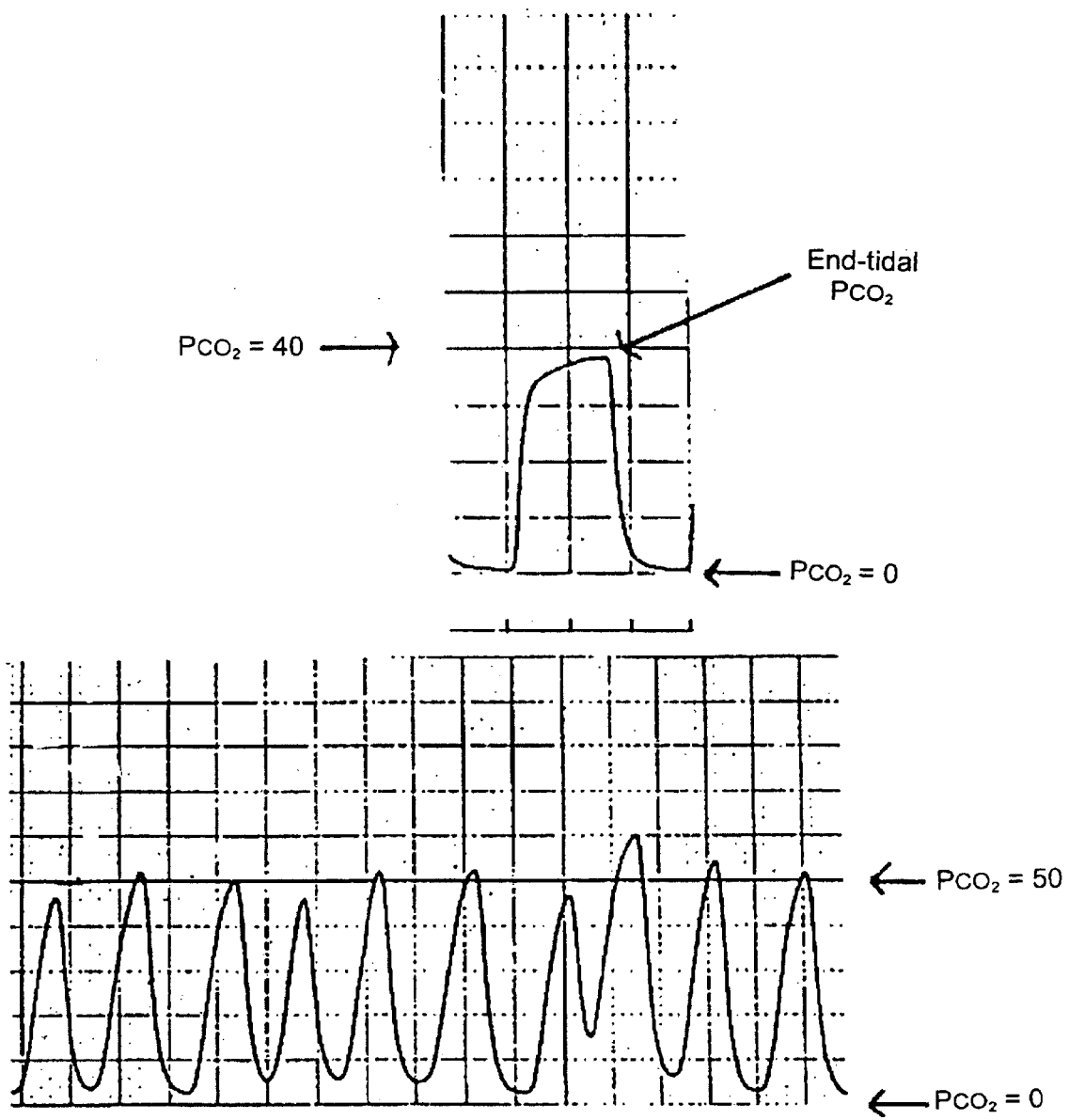
FIG. 3 shows a capnogram of a single respiratory cycle and a capnogram of several breaths from a patient with obstructive lung disease.

Referring now to FIG. 3, the upper frame demonstrates a capnogram of a single respiratory cycle. For accurate blood level correlation, samples are taken at the point labeled "end-tidal $PCO_2$" which reflects the $CO_2$ concentration in the lung. The lower frame shows a capnogram of several breaths from a patient with obstructive lung disease. Again the end-tidal sample correlated best with blood concentration.

Figure 4:
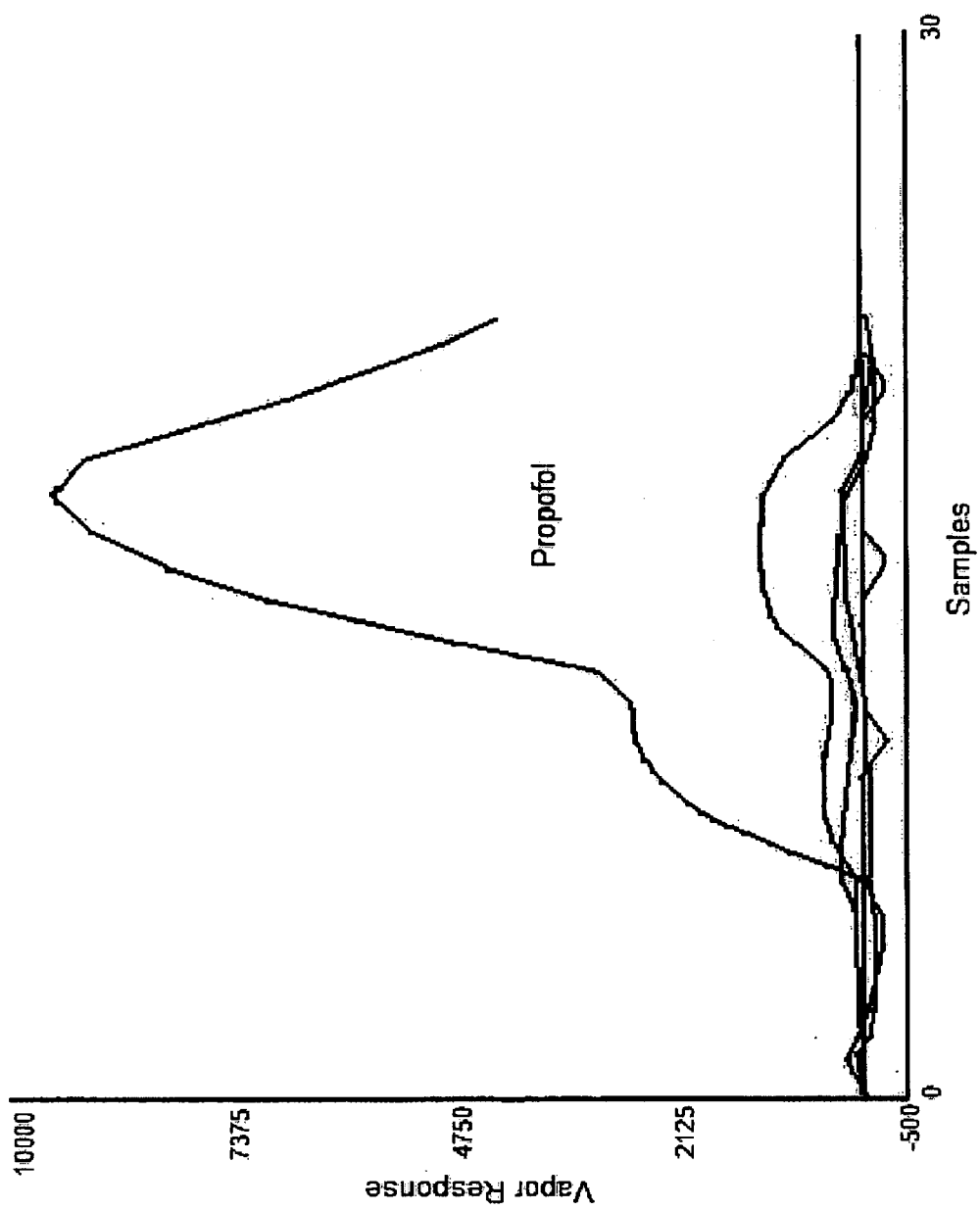
FIG. 4 shows the characteristic "double hump" signature of propofol from a four (4) sensor polymer coated SAW array.

Referring now to FIG. 4, the characteristic "double hump" signature of propofol from a four (4) sensor polymer coated SAW array is shown. In this example, 1 cc of propofol was placed in a "headspace" gas chromatography vial. A 19-gauge hypodermic needle attached to a VaporLab™ gas detector containing the sensor array was inserted into the vial, which was heated to 37° C., and the "signature" was recorded. The VaporLab™ brand instrument is a hand-held, battery powered SAW based chemical vapor identification instrument suitable for detecting vapors in accordance with the present invention. This instrument is sensitive to volatile and semi-volatile compounds having a high-stability SAW sensor array that provides orthogonal vapor responses for greater accuracy and discrimination. The device communicates with computers to provide enhanced pattern analysis and report generation. The device can be easily "trained" to remember chemical vapor signature patterns for fast, "on-the-fly" analysis.

In another embodiment, samples are collected at the distal end of the endotracheal tube (ETT) through a tube with a separate sampling port. This may improve sampling by allowing a larger sample during each respiratory cycle.

The concentration of an anesthetic agent in the body is regulated both by the amount of the agent administered over a given time period and the rate at which the agent is eliminated from the body (metabolism). The present invention provides the steps of administering an agent to the subject and analyzing exhaled breath of the subject for concentration of unbound substances, active metabolites, or inactive metabolites after a suitable time period; the concentration indicates a characteristic of metabolism of the agent in the subject. The method may further include using a flow sensor to detect starting and completion of exhalation. The method further includes providing results from the analysis and controlling the infusion pump for delivering the intravenous anesthesia agent based on the results. Moreover, a CPU may be provided as a data processing/control unit for automatically detecting the signal from the flow sensor to control sampling of exhaled breath. The CPU may further provide the analysis and control of the infusion pump or other administering means.

Methods for administering the agent are readily understood by those skilled in the art. For example, an infusion pump may be used. Compounds may be also administered parenterally, sublingually, transdermally, by i.v. bolus, and by continuous infusion. A number of suitable agents are available for administration as also known by those skilled in the art (Remifentanil—Glaxo Wellcome, Propofol—Zeneca). Agents may also be those of amnesia, analgesia, muscle relaxation, and sedation agents or a combination thereof. Agents may be administered in an amount for analgesia, conscious sedation, or unconsciousness as known in the art. Patient characteristics may also be monitored during administration of the agent.

Concentration in the blood as measured by the breath analysis of the present invention for free agents or metabolites may indicate when the patient is receiving an anesthetic concentration (a high dose), an analgesic concentration (a low dose), or emerging from anesthesia as a result of a level that allows for full recovery. Even if there is wide variation in the metabolism or response to an anesthetic agent, knowledge of the exhaled breath concentration allows the anesthesiologist to know if the drug is accumulating in the blood, possibly leading to a dangerously deep level of anesthesia and/or a prolonged recovery time: or, the concentration is falling, possibly leading to inadequate anesthesia and premature emergence. Monitoring changes in concentration are, therefore, useful.

Figure 1:
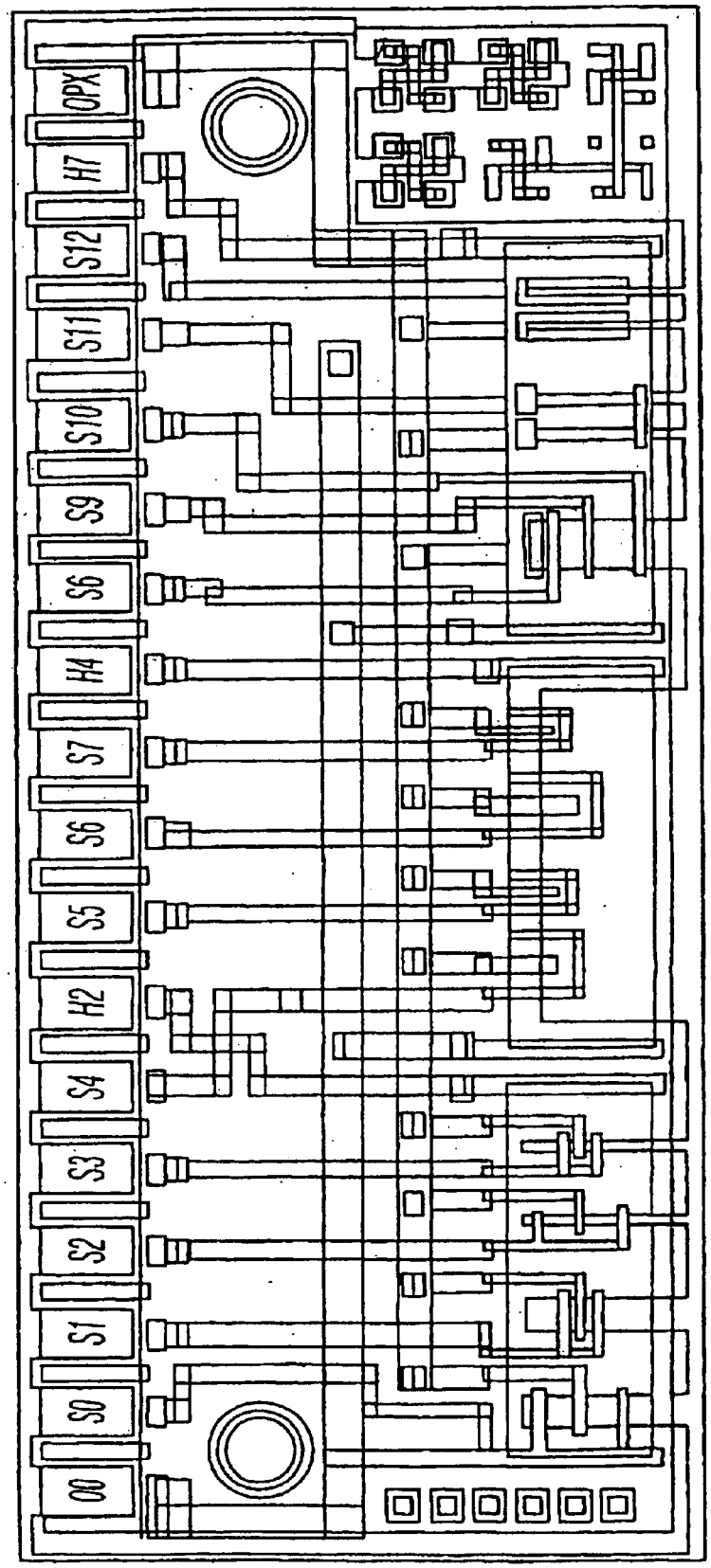
FIG. 1 shows a gas sensor chip that may be utilized as a sensor for the present invention.

In another embodiment, the exhalation air is measured for free agent and/or metabolite concentration either continuously or periodically. From the exhalation air is extracted at least one measured free agent or metabolite concentration value. Numerous types of apparatus may be used to carry out the method of the present invention. In one embodiment, the apparatus includes a conventional flow channel through which exhalation air flows. The flow channel is provided with sensor elements for measuring free agent or metabolite concentration. Furthermore, the apparatus includes necessary output elements for delivering at least a measured concentration result to the operator, if necessary. An alarm mechanism may also be provided. An instrument of similar type is shown in FIGS. 1 and 2 of U.S. Pat. No. 5,971,937 incorporated herein by reference.

In one embodiment, once the level of concentration is measured, it is given numerical value (for example, 50 on a scale of 1 to 100). Should the concentration fall below that value, the new value would be indicative of a decrease in concentration. Should the concentration increase beyond that value, the new value would be indicative of an increase in concentration. This numerical scale would allow for easier monitoring of changes in concentration. The numerical scale would also allow for easier translation into control signals for alarms, outputs, charting, and control of external devices (e.g., infusion pump). The upper and lower limits could be set to indicate thresholds such as from no anesthetic effect to dangerous anesthetic levels.

The invention preferably utilizes gas sensor technology, such as the commercial devices referred to as "artificial noses" or "electronic noses," to non-invasively monitor concentration (FIG. 1). Electronic noses have been used mostly in the food, wine and perfume industry where their sensitivity makes it possible to distinguish between grapefruit oil and orange oil and identify spoilage in perishable foods before the odor is evident to the human nose. There has been little medical-based research and application; however, recent examples demonstrate the power of this non-invasive technique. Electronic noses have determined the presence of bacterial infection in the lungs simply by analyzing the exhaled gases of patients for odors specific to particular bacteria [Hanson C W, Steinberger H A: The use of a novel electronic nose to diagnose the presence of intrapulmonary infection. *Anesthesiology*, V87, No. 3A, Abstract A269, September 1997]. Also a genitourinary clinic has utilized an electronic nose to screen for, and detect bacterial vaginosis, with a 94% success rate after training [Chandiok S, et al.: Screening for bacterial vaginosis: a novel application of artificial nose technology. Journal of Clinical Pathology, 50(9):790–1, 1997]. Specific bacterial species can also be identified with the electronic nose based on special odors produced by the organisms [Parry A D et al.: Leg ulcer odor detection identifies beta-haemolytic streptococcal infection. Journal of Wound Care, 4:404–406, 1995].

A number of patents which describe gas sensor technology include the following: U.S. Pat. No. 5,945,069 to Buchler, entitled "Gas sensor test chip;" U.S. Pat. No. 5,918,257 to Mifsud et al., entitled "Method and devices for the detection of odorous substances and applications"; U.S. Pat. No. 4,938,928 to Koda et al., entitled "Gas sensor"; U.S. Pat. No. 4,992,244 to Grate, entitled "Films of dithiolene complexes in gas-detecting microsensors"; U.S. Pat. No. 5,034,192 to Wrighton et al., entitled "Molecule-based microelectronic devices"; U.S. Pat. No. 5,071,770 to Kolesar, Jr., entitled "Method for gaseous component identification with #3 polymeric film;" U.S. Pat. No. 5,145,645 to Zakin et al., entitled "Conductive polymer selective species sensor;" U.S. Pat. No. 5,252,292 to Hirata et al., entitled "Ammonia sensor;" U.S. Pat. No. 5,605,612 to Park et al., entitled "Gas sensor and manufacturing method of the same;" U.S. Pat. No. 5,756,879 to Yamagishi et al., entitled "Volatile organic compound sensors;" U.S. Pat. No. 5,783,154 to Althainz et al., entitled "Sensor for reducing or oxidizing gases;" and U.S. Pat. No. 5,830,412 to Kimura et al., entitled "Sensor device, and disaster prevention system and electronic equipment each having sensor device incorporated therein," all of which are incorporated herein by reference in their entirety. Other sensors suitable for the present invention include, but are not limited to, metal-insulator-metal ensemble (MIME) sensors, cross-reactive optical microsensor arrays, and fluorescent polymer films, surface enhanced raman spectroscopy (SERS), diode lasers, selected ion flow tubes, proton transfer reaction mass spectrometry, metal oxide sensors (MOS), non-dispersive infrared spectrometer, bulk acoustic wave sensors, colorimetric tubes, infrared spectroscopy (FIG. 2 represents the FT-IR signal for propofol (2,6-diisopropylphenol)).

Recent developments in the field of detection include, but are not limited to, semiconductive gas sensors, mass spectrometers, IR or UV or visible or fluorescence spectrophotometers. The substances change the electrical properties of the semiconductors by making their electrical resistance vary, and the measurement of these variations allows one to determine the concentration of substances. These methods and apparatus used for detecting substances use a relatively brief detection time, of around a few seconds. Other recent gas sensor technologies contemplated by the present invention include apparatus having conductive-polymer gas-sensors ("polymeric") and apparatus having surface-acoustic-wave (SAW) gas-sensors.

The conductive-polymer gas-sensors (also referred to as "chemoresistors") have a film made of a conductive polymer sensitive to the molecules of odorous substances. On contact with the molecules, the electric resistance of the sensors changes and the measurement of the variation of this resistance enables the concentration of the odorous substances to be determined. An advantage of this type of sensor is that it functions at temperatures close to room temperature. One can also obtain, according to the chosen conductive polymer, different sensitivities for detecting different substances.

Polymeric gas sensors can be built into an array of sensors, where each sensor is designed to respond differently to different gases and augment the selectivity of the substances.

The surface-acoustic-wave (SAW) gas-sensors generally include a substrate with piezoelectric characteristics covered by a polymer coating that is able to selectively absorb the substances. The variation of the resulting mass leads to a variation of its resonant frequency. This type of sensor allows for very good mass-volume measures of the substances. In the SAW device, the substrate is used to propagate a surface acoustic wave between sets of interdigitated electrodes. The chemoselective material is coated on the surface of the transducer. When a chemical analyte interacts with a chemoselective material coated on the substrate, the interaction results in a change in the SAW properties such as the amplitude of velocity of the propagated wave. The detectable changes in the characteristics of the wave indicate the presence of the chemical analyte. SAW devices are described in numerous patents and publications, including U.S. Pat. No. 4,312,228 to Wohltjen and U.S. Pat. No. 4,895,017 to Pyke, and Groves Wash., et al.: Analyzing organic vapors in exhaled breath using surface acoustic wave sensor array with preconcentration: Selection and characterization of the preconcentrator adsorbent, *Analytica Chimica Acta* 371 (1988) 131–143, all of which are incorporated herein by reference. Other types of chemical sensors known in the art that use chemoselective coatings applicable to the operation of the present invention include bulk acoustic wave (BAW) devices, plate acoustic wave devices, interdigitated microelectrode (IME) devices, and optical waveguide (OW) devices, electrochemical sensors, optical sensors, and electrically conducting sensors.

Most current technologies for creating large area films of polymers and biomaterials involve the spinning, spraying, or dipping of a substrate into a solution of the macromolecule and a volatile solvent. These methods coat the entire substrate. There are also techniques such as microcontact printing and hydrogel stamping that enable small areas of biomolecular and polymer monolayers to be patterned. Other techniques, such as pulsed laser deposition (PLD), may be used. By this method, a target comprising the stoichiometric chemical composition of the material to be used for the coating is ablated by means of a pulsed laser, forming a plume of ablated material that becomes deposited on the substrate.

Polymer thin films, using a new laser based technique developed by researchers at the Naval Research Laboratory called Matrix Assisted Pulsed Laser Evaporation (MAPLE), have recently been shown to increase sensitivity and specificity of chemoselective Surface Acoustic Wave vapor sensors. A variation of this technique, Pulsed Laser Assisted Surface Functionalization (PLASF) is preferably used to design compound specific biosensor coatings with increased sensitivity for the present invention. PLASF produces similar thin films for sensor applications with bound receptors or antibodies for biosensor applications. By providing improved SAW biosensor response by eliminating film imperfections induced by solvent evaporation and detecting molecular attachments to specific antibodies, high sensitivity and specificity is possible.

Certain extremely sensitive, commercial off-the-shelf (COTS) electronic noses 10, such as those provided by Cyrano Sciences, Inc. ("CSI") (e.g., CSI's Portable Electronic Nose and CSI's Nose-Chip integrated circuit for odor-sensing—U.S. Pat. No. 5,945,069—FIG. 1), maybe used in the method of the present invention to monitor the exhaled breath from a patient. These devices offer minimal cycle time, can detect multiple odors, can work in almost any environment without special sample preparation or isolation conditions, and do not require advanced sensor design or cleansing between tests.

In one embodiment, the device of the present invention may be designed so that patients can exhale via the mouth or nose directly into the device.

Another preferred electronic nose technology of the present invention comprises an array of polymers, for example, 32 different polymers, each exposed to a substance. Each of the 32 individual polymers swells differently to the odor creating a change in the resistance of that membrane and generating an analog voltage in response to that specific substance ("signature"). The normalized change in resistance can then be transmitted to a processor to identify the type, quantity, and quality of the substance based on the pattern change in the sensor array. The unique response results in a distinct electrical fingerprint that is used to characterize the substance. The pattern of resistance changes of the array is diagnostic of the sample, while the amplitude of the pattern indicates the concentration of the sample.

The responses of the electronic nose to specific substances can be fully characterized using a combination of conventional gas sensor characterization techniques. For example, the sensor can be attached to a computer. The results can be displayed on the computer screen, stored, transmitted, etc. A data analyzer can compare a pattern of response to previously measured and characterized responses from known substances. The matching of those patterns can be performed using a number of techniques, including neural networks. By comparing the analog output from each of the 32 polymers to a "blank" or control, for example, a neural network can establish a pattern that is unique to that substance and subsequently learns to recognize that substance. The particular resistor geometries are selected to optimize the desired response to the particular substance being sensed. The sensor of the present invention is preferably a self-calibrating polymer system suitable for liquid or gas phase biological solutions for a variety of substances simultaneously.

The sensor of the present invention might include integrated circuits (chips) manufactured in a modified vacuum chamber for Pulsed Laser Deposition of polymer coatings. It will operate the simultaneous thin-film deposition wave detection and obtain optimum conditions for high sensitivity of SAW sensors. The morphology and microstructure of biosensor coatings will be characterized as a function of process parameters.

The sensor used in the present invention may be modified so that patients can exhale directly into the device. For example, a mouthpiece or nosepiece will be provided for interfacing a patient with the device to readily transmit the exhaled breath to the sensor (See, e.g., U.S. Pat. No. 5,042,501). The output from the neural network of the modified sensor should be similar when the same patient exhales directly into the device and when the exhaled gases are allowed to dry before they are sampled by the sensor.

The humidity in the exhaled gases represents a problem for certain electronic nose devices (albeit not SAW sensors) that only work with "dry" gases. When using such humidity sensitive devices, the present invention may adapt such electronic nose technology so that a patient can exhale directly into the device with a means to dehumidify the samples. This is accomplished by including a commercial dehumidifier or a heat moisture exchanger (HME), a device designed to prevent desiccation of the airway during ventilation with dry gases. Alternatively, the patient may exhale through their nose which is an anatomical, physiological dehumidifier to prevent dehydration during normal respiration. Alternatively, the sensor device can be fitted with a preconcentrator, which has some of the properties of a GC column. The gas sample is routed through the preconcentrator before being passed over the sensor array. By heating and volatilizing the gases, humidity is removed and the compound being measured (analyte) can be separated from potential interferents.

Preferably, in operation, the sensor will be used to identify a baseline spectrum for the patient prior to delivery, if necessary. This will prove beneficial for the detection of more than one drug if the patient receives more than one drug at a time and possible interference from different foods and odors in the stomach, mouth, esophagus and lungs.

Following are examples which illustrate procedures for practicing the invention. These examples should not be construed as limiting. All percentages are by weight and all solvent mixture proportions are by volume unless otherwise noted.

EXAMPLE I

Estimating the Depth of Intravenous Propofol Anesthesia by Measurement of Exhaled Breath Propofol Vapor Concentration The initial intravenous administration of propofol may be either in a bolus of 2 to 5 mg/ml or by a continuous infusion of 25 to 200 mcg/kg/min resulting in a plasma concentration in the 1 to 10 mcg/ml range. The depth of anesthesia (or sedation) achieved depends on patient characteristics as well as the simultaneous use of other drugs such as opioids and nitrous oxide.

For most administrations of propofol at anesthetic depth, the patient's ventilation occurs through a breathing circuit attached to the patient by an external face mask, a laryngeal mask airway (LMA), or by a tube placed in the trachea. These examples of a closed circuit all facilitate positive pressure ventilation if needed, the administration of supplemental inhalation anesthesia with nitrous oxide, and the monitoring of ventilatory adequacy by carbon dioxide measurement. In addition the closed breathing circuit permits side-stream sampling of exhaled breath which can be diverted to the propofol measurement sensor. For non-closed circuit propofol sedation administration, a sampling catheter at the nares or mouth may be used to sample propofol vapor. A simultaneous carbon dioxide measurement may assist in the interpretation of the adequacy of the sampling.

The end-tidal portion of the exhaled breath is that fraction which has equilibrated with the blood returning from the systemic circulation to the lung. For the measurement methods cited below which allow multiple propofol vapor determinations per patient breath, the highest concentrations will be considered end-tidal propofol vapor concentrations. For slower analytical methods, the average exhaled concentrations will be used and corrected using end-tidal-to-average carbon dioxide concentration data. Alternatively, sampling line pressures or carbon dioxide levels may be used to instantaneously define end-tidal gas and direct only this portion of the sample stream to the sensor.

Within the clinical range, the blood level of propofol is directly related to the depth of propofol anesthesia. The blood to end-tidal gradient of propofol is theoretically dependent on four features 1) the vascular-to-alveolar propofol vapor transfer, 2) the matching of pulmonary ventilation to perfusion, 3) the delivery of a mixed alveolar gas sample to the sampling site, and 4) instrumentation accuracy and precision. The vascular-to-alveolar transfer is expected to be stable and predictable due to the small quantities of propofol involved and its highly polar nature. Ventilation-perfusion mismatch should impact propofol measurements less than carbon dioxide measurements due to the comparatively slow time course of propofol blood level changes. Likewise, adequate mixing of the respiratory gas sample by the time it reaches the sampling site should not be a problem compared to carbon dioxide sampling. A calibrated pressurized gas canister of propofol vapor will facilitate automatic recalibration as often as required to maintain sensor accuracy. Due to the relatively slow change of propofol blood levels in clinical work, multiple determinations may be used to improve precision.

The interpretation of the measured end-tidal propofol vapor concentration should emphasize two features: 1) the concentration itself relative to that likely to be required for the clinical scenario, and 2) trending of the propofol vapor concentration over time. The first feature, the magnitude of the concentration itself, may initially reflect incorrect dosing, extremes of age, altered protein binding, or other individual pharmacokinetic deviations. While a range of target propofol vapor concentrations may be expected, individual adjustment of a target level for the clinical scenario is required. Stimulating procedures such as endotracheal intubation, surgical incision, or movement of a fractured limb require a higher range than quiet sedation, anesthesia in a neurologically damaged patient, or anesthesia for a debilitated geriatric patient. The presence of opioids or other anesthetic agents such as nitrous oxide will also lower the target range of propofol vapor concentrations.

The second major feature of the interpretation of end-tidal propofol vapor concentration is trending of the concentration over time. When satisfactory anesthesia is initially established and a propofol infusion is started, an excessive rate of propofol may be inadvertently administered and the blood level may increase well beyond what is necessary and prudent. If the clinical scenario permits a trial reduction of the infusion rate until the patient becomes reactive then an excessive administration rate is ruled out. However, the danger of intraoperative movement in some cases, the simultaneous administration of paralytic agents, or the risk of intraoperative recall may prevent a trial reduction of what may appear to be an appropriate infusion rate. If one could be confident that accumulation of excess propofol in the blood was not occurring at a given rate of infusion as the administration progressed, trial infusion reductions would not be needed. Similarly, if the clearance of propofol in a given patient exceeded the infusion rate, sudden movement or wakefulness could be anticipated and avoided by increasing the infusion rate to maintain the current measured propofol level.

EXAMPLE II

Estimating the Blood Concentration of Supplemental Drugs Administered During Anesthesia and Their Concentration Trends by Measurement in Exhaled Breath. The Opioids Remifentanil and Alfentanil are Discussed as Examples The intravenous administration of remifentanil may be either in a bolus of 0.05 to 1 mcg/kg or by a continuous infusion of 0.0125 to 2 mcg/kg/min resulting in a plasma concentration in the 0.5 to 50 ng/ml range. Similarly, alfentanil, a related opioid, may be administered either in a bolus of 10 to 300 mcg/kg or by a continuous infusion of 0.1 to 15 mcg/kg/min resulting in a plasma concentration in the 10 to 500 ng/ml range. For both drugs the effect achieved depends on the dosage, individual patient characteristics, and the simultaneous administration of other drugs. The wide dosage ranges are a result of a wide range of desired effects; from analgesia during conscious sedation to deep general anesthesia when given to supplement a small dose of a hypnotic agent.

When remifentanil or alfentanil are administered during unconscious sedation or general anesthesia, the patient's ventilation occurs through a breathing circuit attached to the patient by an external face mask, a laryngeal mask airway (LMA), or by a tube placed in the trachea. These examples of a closed circuit all facilitate positive pressure ventilation due to the respiratory depressive effects of opioids, the administration of inhalation anesthetics and oxygen, and the monitoring of ventilatory adequacy by carbon dioxide measurement. In addition the closed breathing circuit permits side-stream sampling of exhaled breath which can be diverted to the remifentanil or alfentanil measurement sensor. For non-closed circuit remifentanil or alfentanil analgesia administration (usually during conscious sedation), a sampling catheter at the nares or mouth may be used to sample exhaled vapor. A simultaneous carbon dioxide measurement may assist in the interpretation of the adequacy of the sampling.

The end-tidal portion of the exhaled breath is that fraction which has equilibrated with the blood returning from the systemic circulation to the lung. For the measurement methods cited below which allow multiple remifentanil or alfentanil vapor determinations per patient breath, the highest concentrations will be considered end-tidal vapor concentrations. For slower analytical methods, the average exhaled concentrations will be used and corrected using end-tidal-to-average carbon dioxide concentration data. Alternatively, sampling line pressures or carbon dioxide concentrations may be used to instantaneously define end-tidal gas and direct only this portion of the sample stream to the sensor.

Within the clinical range, the blood concentration of the opioids remifentanil and alfentanil are directly related to their pharmacodynamic effects. The blood to end-tidal gradient of remifentanil and alfentanil is theoretically dependent on four features 1) the vascular-to-alveolar transfer of the drug, 2) the matching of pulmonary ventilation to perfusion, 3) the delivery of a mixed alveolar gas sample to the sampling site, and 4) instrumentation accuracy and precision. The vascular-to-alveolar transfer is expected to be stable and predictable due to the small quantities of remifentanil or alfentanil involved and its highly polar nature. Ventilation-perfusion mismatch should impact measurements less than carbon dioxide measurements due to the comparatively slow time course of remifentanil and alfentanil blood concentration changes. Likewise, adequate mixing of the respiratory gas sample by the time it reaches the sampling site should not be a problem compared to carbon dioxide sampling. A calibrated pressurized gas canister of the drug vapor will facilitate automatic recalibration as often as required to maintain sensor accuracy. Due to the relatively slow change of blood concentration of these opioids in clinical work, multiple determinations may be used to improve precision.

The interpretation of the measured end-tidal opioid vapor concentration should emphasize two features: 1) the concentration itself relative to that likely to be required for the clinical scenario (in the nanograms per mL of plasma range), and 2) trending of the opioid vapor concentration over time. The first feature, the magnitude of the concentration itself, may initially reflect incorrect dosing, extremes of age, altered protein binding, or other individual pharmacokinetic deviations. While a range of target opioid vapor concentrations may be expected, individual adjustment of a target concentration for the clinical scenario is required. Pharmacologic tolerance and the widely ranging intensity of painful surgical stimuli will alter concentration requirements greatly. The presence of other anesthetic agents such as inhalation anesthetics or regional anesthesia will lower the target range of opioid vapor concentrations.

The second major feature of the interpretation of end-tidal opioid vapor concentration is trending of the concentration over time. After a satisfactory opioid effect is initially established with bolus injections of the remifentanil or alfentanil and a remifentanil or alfentanil infusion is subsequently started, an excessive rate of infusion or drug interactions or low drug metabolism may occur and the blood concentrations may increase well beyond what is necessary and prudent. If the clinical scenario permits a trial reduction of the infusion rate until the patients condition indicates inadequate dosing then an excessive administration rate is ruled out. However, the danger of intraoperative movement in some cases, the simultaneous administration of paralytic agents, or the risk of light anesthesia with intraoperative recall may prevent a trial reduction from what may appear to be an appropriate infusion rate. If one could be confident that accumulation of excess opioids in the blood as reflected in the exhaled breath measurement was not occurring as the administration progressed at a given rate of infusion, trial infusion reductions would not be needed. Similarly, if the clearance of remifentanil or alfentanil in a given patient exceeded the infusion rate, sudden movement or signs of inadequate anesthesia could be anticipated and avoided by increasing the infusion rate to maintain the current measured opioid vapor concentration.

In addition to the rapidly acting opioids remifentanil and alfentanil discussed above, similar exhaled vapor assessment of fentanyl and sufentanil may be clinically useful as an indirect indicator of blood concentrations. Other non-opioid intravenous anesthetics and anesthetic adjuncts such as etomidate, ketamine, and barbiturates (particularly those of short-duration) may also be administered more precisely and safely with monitoring of their exhaled vapor concentrations as a non-invasive rapid estimate of their blood concentration.

EXAMPLE III

Measuring Endogenous and Exogenous Compounds Such as, Ketones and Ammonia in Exhaled Breath Normally, the exhaled breath of a person contains water vapor, carbon dioxide, oxygen, and nitrogen, and trace concentrations of carbon monoxide, hydrogen and argon, all of which are odorless. A common medical problem is halitosis, which is usually caused by the breakdown of food by bacteria producing odorants such as hydrogen sulfide, methyl mercaptan, dimethyl disulphide, indole and others. The sensor technology described herein may be used as a sensitive detector for these odorants and for the diagnosis of tooth decay, gum disease or a variety of oral, pulmonary and sinus conditions.

Other vapor phase compounds include acetone, which is present in diabetics who are in ketoacidosis, ammonia, which is present in patients with liver disease and a variety of odorants which are present in cases of lungs, stomach, gallbladder and kidney dysfunction. Exhaled breath sensing of these compounds may be a highly sensitive method of diagnosing and following the course of treatment of these diseases. The potential for evaluating exhaled breath for markers of carcinoma is being actively explored, and the sensor technology may play a role in this area as well.

One particularly valuable non-invasive test that is based on exhaled breath detection, is the test for *Helicobacter pylori*, the bacterium responsible for stomach ulcers. Subjects are given a 75 mg dose of urea tagged with carbon isotopes to drink and the exhaled breath is evaluated for tagged carbon dioxide. *Helicobacter pylori* secretes the enzyme urease to protect the organism from the acidity of the stomach. The urease breaks down the tagged urea to ammonia and carbon dioxide. While conventional tests measure the tagged carbon dioxide, they are time consuming and expensive. The sensor technology could be used to measure ammonia in the breath quickly and cheaply and alleviate the need to use a radiolabel compound.

Other non-invasive tests for the detection of other pathologic organisms is the gastrointestinal tract and in body fluids can be developed that take advantage of the sensor technology.

EXAMPLE IV

Selection of Sensors

The following are examples of various sensor technologies that may be utilized in practicing the method of the present invention:

Conducting Polymers

Conducting polymer sensors promise fast response time, low cost, and good sensitivity and selectivity. The technology is relatively simple in concept. A conductive material, such as carbon, is homogeneously blended in a specific non-conducting polymer and deposited as a thin film on an aluminum oxide substrate. The films lie across two electrical leads, creating a chemoresistor. As the polymer is subjected to various chemical vapors, it expands, increasing the distance between carbon particles, and thereby increasing the resistance. The polymer matrix swells because analyte vapor absorbs into the film to an extent determined by the partition coefficient of the analyte. The partition coefficient defines the equilibrium distribution of an analyte between the vapor phase and the condensed phase at a specified temperature. Each individual detector element requires a minimum absorbed amount of analyte to cause a response noticeable above the baseline noise. Selectivity to different vapors is accomplished by changing the chemical composition of the polymer. This allows each sensor to be tailored to specific chemical vapors. Therefore, for most applications an array of orthogonal responding sensors is required to improve selectivity. Regardless of the number of sensors in the array, the information from them must be processed with pattern recognition software to correctly identify the chemical vapors of interest. Sensitivity concentration are reportedly good (tens of ppm). The technology is very portable (small and low power consumption), relatively fast in response time (less than 1 minute), low cost, and should be rugged and reliable Electrochemical Sensors Electrochemical sensors rely on an irreversible chemical reaction to measure. They contain an electrolyte that reacts with a specific gas, producing an output signal that is proportional to the amount of gas present. Electrochemical sensors exist for gases such as chlorine, carbon monoxide, hydrogen sulfide, and hydrogen, but cannot be used to measure hydrocarbons. The number of gases that can be detected using this technology is relatively small, but is increasing from year to year.

Electrochemical sensors are excellent for detecting low parts-per-million concentrations. They are also rugged, draw little power, linear and do not require significant support electronics or vapor handling (pumps, valves, etc.) They are moderate in cost ($50 to $200 in low volumes) and small in size.

Gas Chromatography/Mass Spectroscopy (GC/MS)

Gas Chromatography/Mass Spectroscopy (GC/MS) is actually a combination of two technologies. One technology separates the chemical components (GC) while the other one detects them (MS). Technically, gas chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector converts the column eluent to an electrical signal that is measured and recorded. The signal is recorded as a peak in the chromatogram plot. Chromatograph peaks can be identified from their corresponding retention times. The retention time is measured from the time of sample injection to the time of the peak maximum, and is unaffected by the presence of other sample components. Retention times can range from seconds to hours, depending on the column selected and the component. The height of the peak relates to the concentration of a component in the sample mixture.

After separation, the chemical components need to be detected. Mass spectroscopy is one such detection method, which bombards the separated sample component molecules with an electron beam as they elute from the column. This causes the molecules to lose an electron and form ions with a positive charge. Some of the bonds holding the molecule together are broken in the process, and the resulting fragments may rearrange or break up further to form more stable fragments. A given compound will ionize, fragment, and rearrange reproducibly under a given set of conditions. This makes identification of the molecules possible. A mass spectrum is a plot showing the mass/charge ratio versus abundance data for ions from the sample molecule and its fragments. This ratio is normally equal to the mass for that fragment. The largest peak in the spectrum is the base peak. The GC/MS is accurate, selective and sensitive.

Infrared Spectroscopy (FTIR, NDIR)

Infrared (IR) spectroscopy is one of the most common spectroscopic techniques used by organic and inorganic chemists. Simply, it is the absorption measurement of different IR frequencies by a sample positioned in the path of an IR beam. IR radiation spans a wide section of the electromagnetic spectrum having wavelengths from 0.78 to 1000 micrometers (microns). Generally, IR absorption is represented by its wave number, which is the inverse of its wavelength times 10,000. For a given sample to be detected using IR spectroscopy, the sample molecule must be active in the IR region, meaning that the molecule must vibrate when exposed to IR radiation. Several reference books are available which contain this data, including the Handbook of Chemistry and Physics from the CRC Press.

There are two general classes of IR spectrometers—dispersive and non-dispersive. In a typical dispersive IR spectrometer, radiation from a broadband source passes through the sample and is dispersed by a monochromator into component frequencies. The beams then fall on a detector, typically a thermal or photon detector, which generates an electrical signal for analysis. Fourier Transform IR spectrometers (FTIR) have replaced the dispersive IR spectrometer due to their superior speed and sensitivity. FTIR eliminates the physical separation of optical component frequencies by using a moving mirror Michelson interferometer and taking the Fourier transform of the signal.

Conversely, in the non-dispersive IR (NDIR) spectrometer, instead of sourcing a broad IR spectrum for analyzing a range of sample gases, the NDIR sources a specific wavelength which corresponds to the absorption wavelength of the target sample. This is accomplished by utilizing a relatively broad IR source and using spectral filters to restrict the emission to the wavelength of interest. For example, NDIR is frequently used to measure carbon monoxide (CO), which absorbs IR energy at a wavelength of 4.67 microns. By carefully tuning the IR source and detector during design, a high volume production CO sensor is manufactured. This is particularly impressive, as carbon dioxide is a common interferent and has an IR absorption wavelength of 4.26 microns, which is very close to that of CO.

NDIR sensors promise low cost (less than $200), no recurring costs, good sensitivity and selectivity, no calibration and high reliability. They are small, draw little power and respond quickly (less than 1 minute). Warm up time is nominal (less than 5 minutes). Unfortunately, they only detect one target gas. To detect more gases additional spectral filters and detectors are required, as well as additional optics to direct the broadband IR source.

Ion Mobility Spectrometry (IMS)

Ion Mobility Spectrometry (IMS) separates ionized molecular samples on the basis of their transition times when subjected to an electric field in a tube. As the sample is drawn into the instrument, it is ionized by a weak radioactive source. The ionized molecules drift through the cell under the influence of an electric field. An electronic shutter grid allows periodic introduction of the ions into the drift tube where they separate based on charge, mass, and shape. Smaller ions move faster than larger ions through the drift tube and arrive at the detector sooner. The amplified current from the detector is measured as a function of time and a spectrum is generated. A microprocessor evaluates the spectrum for the target compound, and determines the concentration based on the peak height.

IMS is an extremely fast method and allows near real time analysis. It is also very sensitive, and should be able to measure all the analytes of interest. IMS is moderate in cost (several thousand dollars) and larger in size and power consumption.

Metal Oxide Semiconductor (MOS) Sensors

Metal Oxide Semiconductor (MOS) sensors utilize a semiconducting metal-oxide crystal, typically tin-oxide, as the sensing material. The metal-oxide crystal is heated to approximately 400° C., at which point the surface adsorbs oxygen. Donor electrons in the crystal transfer to the adsorbed oxygen, leaving a positive charge in the space charge region. Thus, a surface potential is formed, which increases the sensor's resistance. Exposing the sensor to deoxidizing, or reducing, gases removes the surface potential, which lowers the resistance. The end result is a sensor which changes its electrical resistance with exposure to deoxidizing gases. The change in resistance is approximately logarithmic.

MOS sensors have the advantage of being extremely low cost (less than $8 in low volume) with a fast analysis time (milliseconds to seconds). They have long operating lifetimes (greater than five years) with no reported shelf life issues.

Photo-Ionization Detectors (PID)

Photo-Ionization Detectors rely on the fact that all elements and chemicals can be ionized. The energy required to displace an electron and 'ionize' a gas is called its Ionization Potential (IP), measured in electron volts (eV). A PID uses an ultraviolet (UV) light source to ionize the gas. The energy of the UV light source must be at least as great as the IP of the sample gas. For example, benzene has an IP of 9.24 eV, while carbon monoxide has an IP of 14.01 eV. For the PID to detect the benzene, the UV lamp must have at least 9.24 eV of energy. If the lamp has an energy of 15 eV, both the benzene and the carbon monoxide would be ionized. Once ionized, the detector measures the charge and converts the signal information into a displayed concentration. Unfortunately, the display does not differentiate between the two gases, and simply reads the total concentration of both summed together.

Three UV lamp energies are commonly available: 9.8, 10.6 and 11.7 eV. Some selectivity can be achieved by selecting the lowest energy lamp while still having enough energy to ionize the gases of interest. The largest group of compounds measured by a PID are the organics (compounds containing carbon), and they can typically be measured to parts per million (ppm) concentrations. PIDs do not measure any gases with an IP greater than 11.7 eV, such as nitrogen, oxygen, carbon dioxide and water vapor. The CRC Press Handbook of Chemistry and Physics includes a table listing the IPs for various gases.

PIDs are sensitive (low ppm), low cost, fast responding, portable detectors. They also consume little power.

Surface Acoustic Wave Sensors (SAW)

Surface Acoustic Wave (SAW) sensors are constructed with interdigitated metal electrodes fabricated on piezoelectric substrates both to generate and to detect surface acoustic waves. Surface acoustic waves are waves that have their maximum amplitude at the surface and whose energy is nearly all contained within 15 to 20 wavelengths of the surface. Because the amplitude is a maximum at the surface such devices are very surface sensitive. Normally, SAW devices are used as electronic bandpass filters in cell phones. They are hermetically packaged to insure that their performance will not change due to a substance contacting the surface of the SAW die.

SAW chemical sensors take advantage of this surface sensitivity to function as sensors. To increase specificity for specific compounds, SAW devices are frequently coated with a thin polymer film that will affect the frequency and insertion loss of the device in a predictable and reproducible manner. Each sensor in a sensor array is coated with a different polymer and the number and type of polymer coating are selected based on the chemical to be detected. If the device with the polymer coating is then subjected to chemical vapors that absorb into the polymer material, then the frequency and insertion loss of the device will further change. It is this final change that allows the device to function as a chemical sensor.

If several SAW devices are each coated with a different polymer material, the response to a given chemical vapor will vary from device to device. The polymer films are normally chosen so that each will have a different chemical affinity for a variety of organic chemical classes, that is, hydrocarbon, alcohol, ketone, oxygenated, chlorinated, and nitrogenated. If the polymer films are properly chosen, each chemical vapor of interest will have a unique overall effect on the set of devices. SAW chemical sensors are useful in the range of organic compounds from hexane on the light, volatile extreme to semi-volatile compounds on the heavy, low volatility extreme.

Motors, pumps and valves are used to bring the sample into and through the array. The sensitivity of the system can be enhanced for low vapor concentrations by having the option of using a chemical preconcentrator before the array. In operation, the preconcentrator absorbs the test vapors for a period of time and is then heated to release the vapors over a much shorter time span thereby increasing the effective concentration of the vapor at the array. The system uses some type of drive and detection electronics for the array. An on board microprocessor is used to control the sequences of the system and provide the computational power to interpret and analyze data from the array.

SAW sensors are reasonably priced (less than $200) and have good sensitivity (tens of ppm) with very good selectivity. They are portable, robust and consume nominal power. They warm up in less than two minutes and require less than one minute for most analysis. They are typically not used in high accuracy quantitative applications, and thus require no calibration. SAW sensors do not drift over time, have a long operating life (greater than five years) and have no known shelf life issues. They are sensitive to moisture, but this is addressed with the use of a thermally desorbed concentrator and processing algorithms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for determining the blood level concentration of at least one agent selected from the group consisting of anesthetics, analgesics, muscle relaxants, sedatives, and anxiolytics, wherein the agent is administered into a patient's bloodstream, comprising:
   sampling a patient's expired breath;
   analyzing the breath for concentration of at least one substance indicative of the agent using sensor technology;
   determining at least one blood level concentration based on the concentration of at least one substance indicative of the at least one agent; and
   using a flow sensor to detect starting and completion of exhalation during said sampling step.

2. The method of claim 1 wherein the breath is analyzed after a predetermined period of time.

3. The method of claim 1 further comprising the step of controlling an infusion pump for delivering the agent intravenously based on the determined blood level concentration.

4. The method of claim 1 wherein the agent is delivered by a delivery method selected from the group comprising: intravenous continuous delivery, parenteral delivery, sublingual delivery, transdermal delivery, and intravenous bolus delivery.

5. The method of claim 1 wherein the agent is delivered by continuous infusion.

6. The method of claim 1 wherein the agent is delivered by an infusion pump.

7. The method of claim 1 wherein the agent is selected from the group comprising Remifentanil and Propofol.

8. The method of claim 1 wherein the steps are repeated periodically to monitor trending over time.

9. The method of claim 1 wherein the agent is for amnesia.

10. The method of claim 1 wherein the agent is for analgesia.

11. The method of claim 1 wherein the agent is for muscle relaxation.

12. The method of claim 1 wherein the agent is for sedation.

13. The method of claim 1 wherein a combination of agents is administered.

14. The method of claim 1 wherein the determined blood level concentration is measured to determine anesthetic blood concentration.

15. The method of claim 1 wherein the determined blood level concentration is measured to determine analgesic blood concentration.

16. The method of claim 1 wherein the determined blood level concentration is measured for alevel indicative of recovery.

17. The method of claim 1 wherein the sampling is continuous.

18. The method of claim 1 wherein the sampling is periodic.

19. The method of claim 1 wherein the patient's breath is analyzed by sensor technology selected from semiconductor gas sensor technology, conductive polymer gas sensor technology, or surface acoustic wave gas sensor technology.

20. The method of claim 19 wherein the sensor technology produces a unique electronic fingerprint to characterize the concentration of said at least one substance.

21. The method of claim 1 further comprising the step of recording data resulting from analysis of the patient's breath.

22. The method of claim 1 further comprising the step of transmitting data resulting from analysis of the patient's breath.

23. The method of claim 1 wherein the analysis of the patient's breath includes comparing the substance sensed in the patient's breath with a predetermined signature profile.

24. The method of claim 1 further comprising the step of capturing the patient's breath in a vessel prior to analysis.

25. The method of claim 1 further comprising the step of dehumidifying the patient's breath prior to analyzing.

26. The method of claim 1 wherein said analysis further includes detecting exhalation of the patient's breath with a sensor.

27. The method of claim 1 wherein said substance indicative of the agent is free agent.

28. The method of claim 1 wherein said substance indicative of the agent is metabolites of the agent.

29. The method of claim 1 wherein said substance indicative of the agent is free agent and metabolites of the agent.

30. The method of claim 1 further comprising the step of assigning a numerical value to the concentration of at least one substance indicative of the agent as analyzed upon reaching a level of pharmacological effect in said patient and, thereafter, assigning higher or lower values to the concentration based on its relative changes.

31. The method of claim 30 further comprising monitoring the concentration of at least one substance indicative of the agent by monitoring changes in said value and adjusting administration of said agent to maintain a desired pharmacological effect.

32. An apparatus for administering intravenous anesthesia to a patient comprising:
   at least one supply of at least one intravenous anesthesia agent;
   intravenous delivery means for controllably intravenously delivering said at least one intravenous anesthesia agent to the patent;
   a breath analyzer for analyzing the patient's breath for concentration of at least one substance indicative of the anesthetic agent in the patient's bloodstream and providing a signal to indicate the anesthetic agent concentration delivered to the patient; and a system controller connected to the intravenous delivery means which receives the signal and controls the amount of anesthetic agent based on the signal.

33. A method for monitoring perflubron levels in an anemic patient, comprising:

(i) sampling a patient's breath;

(ii) analyzing the breath for concentration of perflubron using sensor technology; and (iii) calculating the blood concentration of perflubron based on the concentration.

* * * * *

UNITED STATES PATENT AND TRADEMARK OFFICE
CERTIFICATE OF CORRECTION

PATENT NO. : 7,104,963 B2  
APPLICATION NO. : 10/054619  
DATED : September 12, 2006  
INVENTOR(S) : Richard J. Melker and David Bjoraker It is certified that error appears in the above-identified patent and that said Letters Patent is hereby corrected as shown below:

Column 19,  
Line 34, "substrance" should be --substance--.

Column 20,  
Line 6, "for alevel indicative of" should read --for a level indicative of--.

Column 20,  
Line 24, "transmitting data" should read --transmitting or displaying data--.

Signed and Sealed this

Thirteenth Day of February, 2007

JON W. DUDAS  
*Director of the United States Patent and Trademark Office*